United States Patent [19]
Vinayagamoorthy et al.

[11] Patent Number: 5,994,528
[45] Date of Patent: Nov. 30, 1999

[54] METHOD OF DETECTING GENE EXPRESSION AND/OR OF PREVENTING SUCH EXPRESSION IN CELLS

[76] Inventors: Thuraiayah Vinayagamoorthy, 112-245 Stillwater Dr., Chalsea Gardens, Saskatoon, Saskatchewan, Canada, S7J 4M7; Eric Schloss, #304, 8215-112 St., Edmonton, Alberta, Canada, T6G 2C8

[21] Appl. No.: 09/038,014

[22] Filed: Mar. 11, 1998

Related U.S. Application Data

[62] Division of application No. 08/929,302, Sep. 11, 1997.

[60] Provisional application No. 60/027,370, Sep. 24, 1996.

[51] Int. Cl.$^6$ .......................... C07H 21/02; C07H 21/04; C12P 19/301; C12Q 1/68
[52] U.S. Cl. .................. 536/24.3; 536/24.31; 536/24.32; 536/23.1; 536/24.5; 435/6; 435/91.2; 435/91.5
[58] Field of Search .................................. 536/24.3, 23.1, 536/24.31, 24.32, 24.33, 24.5; 435/6, 91.2, 91.5

[56] References Cited

U.S. PATENT DOCUMENTS

| | | | |
|---|---|---|---|
| 5,585,479 | 12/1996 | Hoke et al. | 536/24.5 |
| 5,593,829 | 1/1997 | McCabe et al. | 435/6 |
| 5,595,872 | 1/1997 | Wetterau, II et al. | 435/6 |

OTHER PUBLICATIONS

Ørum et al, "Single base pair mutation analysis by PNA directed PCR clamping," Nucleic Acids Research, vol. 21, No. 23, pp. 5332–5336. Date: 1993.

Herrmann et al, "PCR and reverse dot Hybridization for the detection of endogenous retroviral transcripts," Journal of virological Methods 46, Elsevier Science B.V., pp. 333–348. Date: 1994.

Probst et al, "G–tetrad in antisense targeting," Trends Genetics 12(8):90–91. Date: 1996.

Harris et al, "Strategies for targeted gene therapy," Trends Genetics 12(10):400–405. Date: 1996.

Marshall, "Gene therapy's growing pains," Science 269:1050–1055. Date: Aug. 1995.

Kawasaki, "Amplification of RNA" in PCR Protocols: A guide to Methods and Applications, Innis et al, Eds., pp.21–27. Date: 1990.

Gibbs et al, "Structure, polymorphism and novel repeated DNA elements revealed by a complete sequence of the human alpha fetoprotein gene" Biochemistry 26:1332–1343, 1987.

Kan et al, "Proton nuclear magnetic resonance studies on dideoxyribonucleoside methylphosphonates", Biochemistry 19:2122–2132, 1980.

*Primary Examiner*—W. Gary Jones
*Assistant Examiner*—Jeffrey Fredman

[57] ABSTRACT

A method of amplifying a nucleotide sequence complementary to an mRNA template derived from genomic DNA. The method involves the following steps. A sample mixture containing an mRNA template and corresponding genomic DNA is provided, the genomic DNA including at least two exons separated by at least one intron. A pair of intron-blockers are introduced into the mixture, the intron-blockers comprising a sequence of intron-specific oligonucleotides modified to prevent nucleotide extension in conditions promoting polymerase chain reaction. A primer pair promoting amplification of cDNA derived from the mRNA template is introduced into the mixture and then reverse transcription polymerase chain reaction is carried out to amplify cDNA. Detection of the cDNA is proof of the existence of mRNA in the sample, and thus proof of expression of the corresponding gene. The method avoids false positives caused by amplification of genomic DNA as well as cDNA based on an mRNA template. The invention includes a method of suppressing gene expression in vivo, which comprises exposing cells containing a gene to be suppressed, made up of exons and at least one intron, to intron-blockers having nucleotide sequences that bind to the intron to prevent gene expression.

4 Claims, 9 Drawing Sheets

Amplification of genomic DNA

Bases

Sugar-phosphate backbone

5'end of polynucleotide chain

```
                        SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Human Alpha Feto Gene (xi) SEQUENCE DESCRIPTION: SEQ ID NO:1:

GAAGAGCTAT TGTATGAAAG AGGGA                                            25

(2) INFORMATION FOR SEQ ID NO:2:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Human Alpha Feto Gene (xi) SEQUENCE DESCRIPTION: SEQ ID NO:2:

CCCTCCCTGT GTCCATGAAA CATGG                                            25

(2) INFORMATION FOR SEQ ID NO:3:
```

(i) SEQUENCE CHARACTERISTICS:
        (A) LENGTH: 800 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human Alpha Feto Gene (ix) FEATURE:
        (A) NAME/KEY: exon
        (B) LOCATION: 1..133

(ix) FEATURE:
        (A) NAME/KEY: intron
        (B) LOCATION: 134..702

(ix) FEATURE:
        (A) NAME/KEY: exon
        (B) LOCATION: 703..800

(ix) FEATURE:
        (A) NAME/KEY: primer_bind
        (B) LOCATION: 2..22

(ix) FEATURE:
        (A) NAME/KEY: primer_bind
        (B) LOCATION: 775..798

(ix) FEATURE:
        (A) NAME/KEY: misc_binding
        (B) LOCATION: 335..355

(ix) FEATURE:
        (A) NAME/KEY: misc_binding
        (B) LOCATION: 281..303

(xi) SEQUENCE DESCRIPTION: SEQ ID NO:3:

```
TTTTGTTCAT GAATATTCAA GAAGACATCC TCAGCTTGCT GTCTCAGTAA TTCTAAGAGT    60

TGCTAAAGGA TACCAGGAGT TATTGGAGAA GTGTTTCCAG ACTGAAAACC CTCTTGAATG   120

CCAAGATAAA GGAGTAAGTT GCTCTAGAAT TTTAGGGGAG TATGAAAAAC TGGATTGATA   180

TCATCTGTTA AAAATGCTGT TGTTTGAAA GCCTCTAGTT TCAACTAGT TGTTAGCCAG     240

TTATATCTAT TTGTCTAGAT ATTAAGCTGT TATTAACTAG CAGTCAGCAG CTAGTGGCTT   300

GTCTTTAGAA ACAAAAATGT TAATTGCTTC TCAGCCTTTT GGCTAAGATC AAGTGTAGAA   360

ATAAAAATGT TAACCAAAAG TCCTTTGATC CACAAATAAA GGTAGTATTC ATTATTCATT   420

TTTGGATAAC TTCAGAAAGG CAAGAATTTG GTACAGAAAG AACTGTAACC ATTTATCCAA   480

AGATTGAGTT TTGCCATTAA ATGATTTTGT GATTTATAAA ATGTTAAACT TAATCTCCCC   540

AAAATCCATT TTCTGTAATT ATCAAAATTT ACACTTTACC ATATTTAATA TTTAAACATC   600

TCTGATTGGT TTTATAATAG TATATAATAT TGATCAATTT TATATACAAA GTTATGCATC   660

CAAGAAAAGA AAAATGTATA TGTAATAATT CTTCATTTTC AGGAAGAAGA ATTACAGAAA   720

TACATCCAGG AGAGCCAAGC ATTGGCAAAG CGAAGCTGCG GCCTCTTCCA GAAACTAGGA   780

GAATATTACT TACAAAATGC                                              800
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human Alpha Feto Gene (xi) SEQUENCE DESCRIPTION: SEQ ID NO:4:

CAGTCAGCAG CTAGTGGCTT GC                                            22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human Alpha Feto Gene (xi) SEQUENCE DESCRIPTION: SEQ ID NO:5:

CACTTGATCT TAGCCAAAAG GC                                            22

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Human Alpha Feto Gene (xi) SEQUENCE DESCRIPTION: SEQ ID NO:6:

TTTGTTCATG AATATTCAAG AAGA                                          24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Human Alpha Feto Gene (xi) SEQUENCE DESCRIPTION: SEQ ID NO:7:

ATTTTGTAAG TAATATTCTC CTAG                    24

METHOD OF DETECTING GENE EXPRESSION AND/OR OF PREVENTING SUCH EXPRESSION IN CELLS

This application is a division of application Ser. No. 08/929,302, filed Sep. 11, 1997.

CROSS-REFERENCE TO RELATED APPLICATION

This application is a continuation-in-part of prior US provisional patent application Serial No. 60/027,370 (pending) filed Sep. 24, 1996.

BACKGROUND OF THE INVENTION

I. Field of Invention

The present invention relates to a method of detecting gene expression in cells and, if desired, of preventing such expression. More particularly, the invention relates to methods of detecting mRNA in the presence of complementary genomic DNA, and of preventing the expression of such complementary DNA. The invention also relates to specific testing or identification procedures using such methods.

II. Description of the Prior Art

Specific gene expression or the lack thereof can be indicative of a genetic defect, a disease marker or a viral infection. Therefore, it is routinely desirable to investigate the expression of specific genes. mRNA is produced in cells during gene translation to form a corresponding protein, so the detection of a particular mRNA in a cell is evidence of activation of the corresponding gene. In other words, if mRNA is present in a cell, it may be assumed that gene expression is taking place.

It is possible to detect mRNA by means of the polymerase chain reaction (PCR) that is used to amplify the miniscule amounts of mRNA present to provide quantities suitable for detection and/or identification. This is possible because PCR is capable of achieving amplification rates in excess of a millionfold.

The protocol for the polymerase chain reaction has been known for several years and has achieved widespread application in the fields of medical diagnostics and forensics. U.S. Pat. Nos. 4,683,202 and 4,683,195, for example, describe the original PCR process for the amplification and detection of nucleic acid sequences. The basic principle of PCR relies on the repetition of the following steps:

1) Denaturation—the template strands of the originating DNA sample are subjected to elevated temperatures and are subsequently denatured to form single stranded DNA templates.

2) Renaturation—oligonucleotide primers complementary to regions flanking a gene or other DNA sequence of interest are hybridized to the single stranded DNA templates at the 3'-ends of the template sequence at an optimally lower temperature.

3) Synthesis—thermostable DNA polymerase present in the sample mixture functions to extend the oligonucleotide primers from the 3'-ends with nucleotide triphosphates complimentary to the template nucleotide sequence.

4) Repetition—the above steps are repeated many times. Each time the denaturation step is completed, DNA strands newly formed in the preceding step are released as single stranded DNA templates for the subsequent steps, thus increasing the copies of the sequence of interest exponentially as the repetitions progress.

With continued use, the basic PCR technique has been modified or extended in various ways. Advancements in the field of PCR technology are described, for example, in U.S. Pat. Nos. 5,436,149, 5,405,774, 5,340,728 and 5,338,671. One of the ways in which PCR has been extended is to embrace the use of mRNA as a template for nucleotide sequence amplification. This is discussed, for example, in U.S. Pat. Nos. 5,407,800, 5,322,770 and 5,527,669, wherein cDNA is first synthesized from an mRNA template by reverse transcription and subsequently amplified by PCR. Reliant on the activity of an enzyme, reverse transcriptase (RT), deoxyribonucleotides complementary to an mRNA template are directed into a growing cDNA strand.

In-situ PCR techniques involving reverse transcriptase (RT-PCR) have been developed to detect levels of particular mRNAs in cells. However, limitations have been encountered with this approach when the primer pair introduced to initiate amplification of the cDNA template also amplifies the corresponding region of the genome, thus generating false positive results. The detection of a gene in the genome does not, of course, mean that the gene is being expressed, but merely that it is present.

In attempt to overcome this imprecision, techniques have been adopted to eliminate the genomic DNA by digestion in the presence of a DNase enzyme prior to initiation of reverse transcription. This digestion step, as presently used, takes at least seven hours for completion and creates additional problems, such as the following:

1) it limits the use of this technique for routine medical application which require more rapid results; and 2) it adds an element of uncertainty as the procedure lacks an indicator of complete removal of the genomic DNA.

There is therefore a need for an improved procedure for the detection of gene expression involving in-situ PCR to overcome the false positive problem while avoiding disadvantages of known procedures, such as those mentioned above.

SUMMARY OF THE INVENTION

An object of the present invention is to provide a method of reliably detecting gene expression in cells.

Another object of the invention is to prevent the expression of genomic DNA, when desired.

Another object of the present invention is to provide an improved method of conducting in-situ PCR in which mRNA/cDNA is employed as a template.

Another object of the invention is to provide a method of in-situ PCR that avoids false results caused by expression of genomic DNA.

Another object of the invention is to provide a method of amplifying and identifying or detecting mRNA that can be carried out rapidly and accurately.

Another object of the invention is to provide a method for accurate and efficient detection of the expression of specific mRNA in eukaryotic cells in the presence of an intact genome for advancement in the field of diagnostics.

According to one aspect of the present invention, there is provided a method of amplifying a nucleotide sequence complementary to an mRNA template derived from genomic DNA, which comprises providing a sample mixture containing an mRNA template and corresponding genomic DNA, said genomic DNA including at least two exons separated by at least one intron, introducing intron-blockers into said mixture, said intron-blockers comprising a sequence of intron-specific oligonucleotides modified to prevent nucleotide extension in conditions promoting polymerase chain reaction, and carrying out reverse transcription polymerase chain reaction on said mRNA template, to amplify said cDNA, in the presence of a polymerase and a primer pair promoting amplification of cDNA derived from said mRNA template.

By the term "intron-blocker" as used in the present application, we mean a molecule that is capable of binding to (annealing with) a target intron in genomic DNA without also binding to exon DNA, and that is capable of preventing replication of a transcription region of the genomic DNA incorporating said intron. The intron-blockers are normally used in pairs to block equivalent regions of the introns of complementary strands of the genomic DNA.

As a component of the PCR mixture, the primers for RT-PCR are oligonucleotides that are capable of acting as points of initiation of DNA synthesis when placed under conditions in which synthesis of a primer extension product complementary to a nucleic acid strand is induced. Such conditions include the presence of deoxyribonucleotides (such as the four standard deoxyribonucleoside-5'-triphosphates), a thermostable DNA polymerse, and suitable temperature, pH and cofactor. The primers may be labelled with a fluorescent marker according to any known method, e.g. the fluorescent-labelled nucleotide may be transferred to the 5'-end of the PCR primer using $T_4$ polynucleotide kinase.

According to a particularly preferred form of the present invention, the in-situ RT-PCR preferably follows in accordance to the following steps:

1) Fixation of cells or tissues—isolate target cell/tissue for amplification/identification.
2) Pepsin digestion—disruption of cytoplasmic membrane, making holes for the reagents to enter the cells, while retaining the integrity of the cell wall.
3) Reverse transcription—construct an mRNA derived cDNA template.
4) Polymerase reaction—wherein the PCR mixture includes modified oligonucleotides as intron-blockers and PCR primers, the primers preferably incorporating a fluorescent label or other identification means.
5) Detection by visualizing a fluorescent signal or by other means. Positive detection indicates the presence of mRNA and thus confirms gene expression. Depending on the particular test, this may be indicative of a genetic defect, a specific protein, viral infection, disease specific marker, etc.

According to another aspect of the invention there is provided a method of detecting a specific mRNA derived from genomic DNA, which comprises providing a sample mixture potentially containing an mRNA template and corresponding genomic DNA, said genomic DNA including at least two exons separated by at least one intron, introducing intron-blockers into said mixture, said intron-blockers comprising a sequence of intron-specific oligonucleotides modified to prevent nucleotide extension in conditions promoting polymerase chain reaction, carrying out reverse transcription polymerase chain reaction to amplify said cDNA, introducing a primer pair promoting amplification of cDNA derived from said mRNA, and detecting amplified cDNA as a confirmation of mRNA in said sample mixture.

According to yet another aspect of the invention there is provided a method of distinguishing fetal cells from maternal cells in a sample taken from a pregnant female, comprising providing a sample potentially containing fetal cells or maternal cells, preparing said sample for reverse transcriptase polymerase chain reaction, introducing intron-blockers into said prepared sample, said intron-blockers comprising oligonucleotides modified to prevent nucleotide extension in conditions promoting polymerase chain reaction, and having sequences complementary to intron regions of an alpha feto protein gene; introducing a primer pair promoting amplification of cDNA derived from mRNA transcribed from said alpha feto protein gene, carrying out reverse transcription polymerase chain reaction to amplify said cDNA, and detecting amplified cDNA as a confirmation of a presence of said alpha feto protein gene as confirmation that said cells are fetal cells and hence distinguish the fetal cells from maternal cells.

According to the methods of the invention mentioned above, the amplification of genomic DNA during the polymerase chain reaction is avoided because of the intron-specific, non-extending blockers annealed thereto, therefore allowing only the amplification of the reverse transcription template (an mRNA derived cDNA template). Preferably, the intron-blockers used for this purpose are oligonucleotides having sequences that are complementary to an intron region of the genomic DNA, but are modified to prevent chain extension (polymerisation) in PCR conditions.

The intron-blockers are consequently similar to primers used for PCR except that they are intron-specific (they do not bind to cDNA) and are modified to prevent extension. The use of such modified oligonucleotide intron-blockers thus provides a means for preventing the amplification of genomic DNA during in-situ PCR.

The intron-blockers developed for the improvement of in situ RT-PCR may also be used in other applications not necessarily involving PCR. For example, the intron-blockers may be used to prevent the expression of genes in vivo in cases of gene therapy. By subjecting living cells to exposure to intron-blockers, the genes may be "turned off" (expression prevented) since the fact that the intron-blockers bind to introns present in genes means that the genes cannot be expressed.

The transcript (mRNA) of a gene is a linear assembly of the relevant exons of that gene. The nucleotide sequence of the transcript has homology to many functional motifs, e.g. Phosphokinase C activity (PKC activity). Though the transcript (mRNA) carries this functional motif, the biological role of the gene product (protein) may not be related to PKC activity. If a blocker were designed based on the exon sequence of the gene, it might block the expression of other transcripts which were not intended to be blocked. Therefore, the advantage of using intron blockers is that there is little or no chance of interference with the expression of any transcript.

The ability to prevent the expression of particular genes in this way is advantageous in the case of gene therapy, for example by blocking the expression of cell division-associated genes (e.g. for the treatment of cancers such as leukemia), the expression of oncogenes or proto-oncogenes, e.g. c-fos, c-junc, or the suppression of defective genes (e.g. genes causing sickle-cell anaemia).

Thus, according to a further aspect of the invention, there is provided a method of suppressing gene expression in vivo, which comprises exposing cells containing a gene to be suppressed, made up of exons and at least one intron, to intron-blockers having nucleotide sequences that bind to said at least one intron to prevent gene expression.

It will be realized from the description above that the invention, in its broadest aspect, includes any and all methods by which one or more introns of genomic DNA can be "blocked" (i.e. prevented from undergoing amplification) by suitable annealing or attaching molecules that do not adversely affect PCR amplification of the corresponding mRNA/cDNA template when such amplification is used.

DETAILED DESCRIPTION OF THE INVENTION

Gene expression can be described as the "turning on" of certain factors which initiate the transcription (mRNA synthesis) and subsequent translation (protein synthesis) of a specific gene. Alternatively, gene expression can be viewed as an interpretation of the genetic information contained within a gene. If a gene is expressed, transcriptional factors will direct the production of an mRNA copy of the DNA template.

Figure 1:
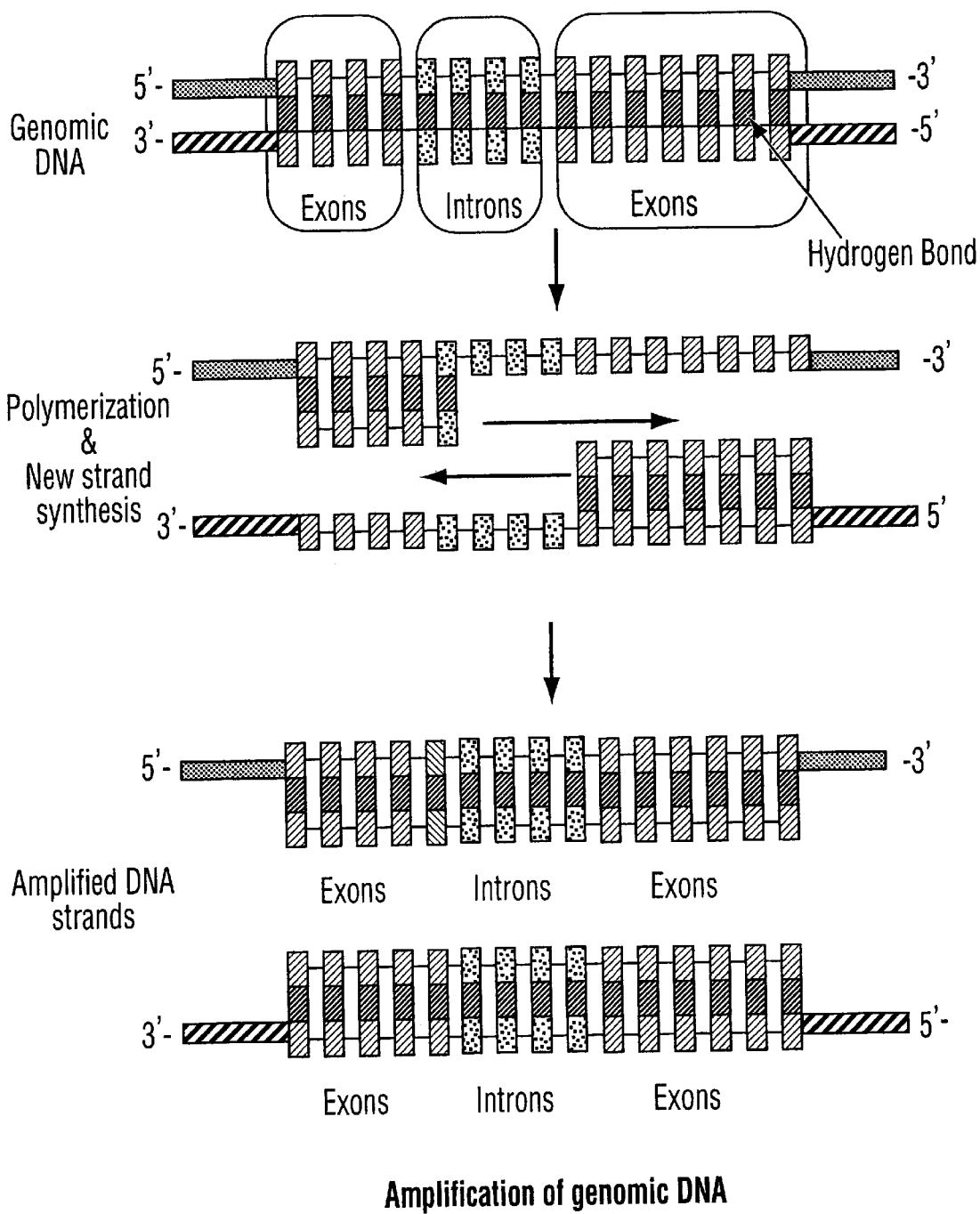
FIG. 1 is a schematic representation of genomic DNA illustrating the steps of DNA denaturing, polymerization and amplification.

Eukaryotic genes comprise two regions, namely introns and exons. An intron is a non-coding intervening sequence located along the parent DNA, whereas an exon is a part of the coding sequence of the gene wherein all regions or parts of the gene are amplified. Genomic DNA can be amplified by PCR to produce numerous additional copies. FIG. 1 illustrates such amplification of genomic DNA by PCR, wherein all regions of the gene are amplified, including the indicated non-coding intron sequence.

Figure 2:
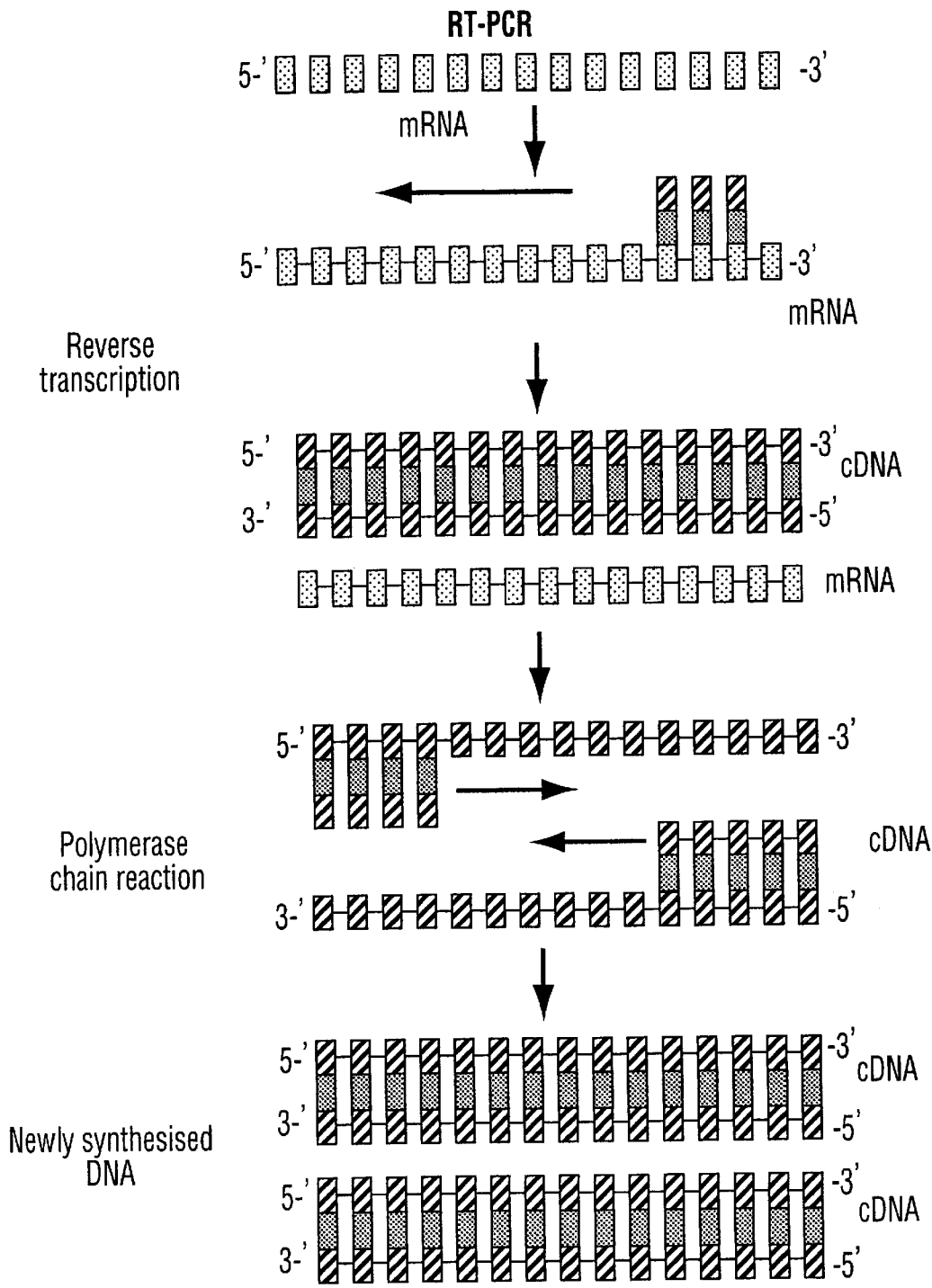
FIG. 2 is a schematic representation showing various stages of reverse transciptase PCR by which cDNA is amplified from an mRNA template.

A eukaryotic cell has the ability to remove introns from the transcribed mRNA, leaving an mRNA based only on the assembled exons of the parent DNA. This mRNA construct contains a continuum of coding information representative of gene expression and therefore is the desirable target for detection since it is formed only during gene expression. Reverse transcription provides a cDNA copy of the mRNA template, which can be further amplified by PCR and labelled for detection (as shown in FIG. 2).

In at least a preferred form, the present invention introduces modified intron-specific oligonucleotides (referred to herein as intron-blockers—i.e. oligonucleotides having base sequences complementary to at least part of an intron sequence not also found in an exon) to the reaction medium during (or prior to) in-situ PCR detection of mRNA. These oligonucleotides have been modified so that they do not undergo chain extension in PCR conditions, and preferably also resist nucleotide replacement (exonuclease activity).

Figure 3:
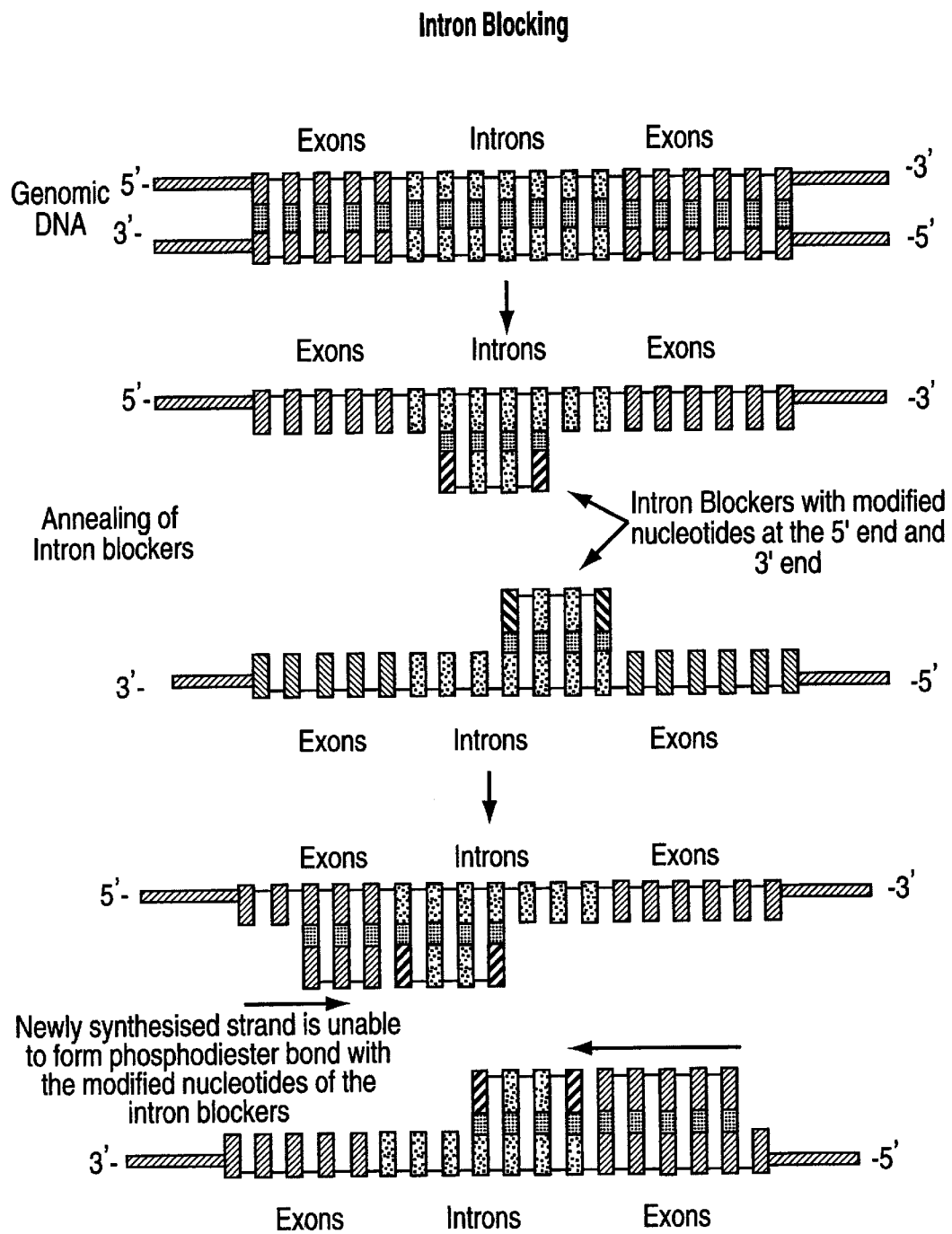
FIG. 3 is a schematic representation similar to FIG. 1, illustrating how the presence of modified introns prevents the transcription of genomic DNA during PCR.

As shown in FIG. 3, the modified oligonucleotides anneal exclusively to target intron regions of the genome, functioning to block the amplification of genomic DNA during the PCR procedure. Since the target mRNA produced during gene expression does not include sequences corresponding to the introns, reverse transcription of the mRNA sequence and amplification of the resulting cDNA sequence is not prevented by the presence of the intron-specific oligonucleotides in the PCR medium. As with conventional PCR, a primer pair is incorporated in the reaction medium to target the coding regions of interest at a specific stage of protein synthesis and to initiate the amplification of the mRNA derived cDNA template for detecting specific mRNA expression.

In short, therefore, the strategy of the present invention, at least in one of its forms, is to block the replication of the genomic DNA in performing in-situ PCR by blocking at least one intron, taking advantage of the fact that introns are found only in the genomic DNA and not in the target mRNA. This strategy is achieved by the introduction of a pair of modified non-extending oligonucleotides (so-called "intron-blockers") complementary to the intron region (non-coding) of the gene of interest on the parent (genomic) DNA.

A suitable pair of modified oligonucleotides complimentary to the intervening intron regions of the parent DNA may be synthesized according to any method known in the art. DNA synthesis is quite simple in concept. A reactive 3' phosphorous group of one nucleoside is coupled to the 5' hydroxyl of another nucleoside. The former is a monomer, delivered in solution. The latter is immobilized on a solid support. An internucleotide linkage is thus formed. Three other chemical reactions are necessary to prepare the growing chain of DNA for the next coupling. In this way, a synthesis cycle is conducted, adding one nucleoside monomer at a time. This may be carried out in a DNA synthesiser, many examples of which are commercially available.

The desired sequence and length are defined by the operator on the synthesizer. When the chain is complete, the crude DNA (oligonucleotide) must be cleaved from the support and deprotected.

The phosphoramidite method of oligonucleotide synthesis is the chemistry of choice for most laboratories because of efficient and rapid coupling and the stability of the starting materials. The synthesis is performed with the growing DNA chain attached to a solid support so that excess reagents, which are in the liquid phase, can be removed by filtration. Therefore, no purification steps are required between cycles. This support material is a form of silica, controlled-pore-glass (CPG) beads. The particle size and the pore size have been optimized for liquid transfer and mechanical strength in the synthesis cycle. The starting material is the solid support derivatized with the nucleoside, which will become the 3'-hydroxyl end of the oligonucleotide. The nucleoside is bound to the solid support through a linker attached at the 3'-hydroxyl. The 5'-hydroxyl is blocked with a dimethoxytrityil (DMT) group.

The first step of the synthesis cycle is treatment of the derivatized solid support with acid to remove the DMT group. This frees the 5'-hydroxyl for the coupling reaction.

An activated intermediate is created by simultaneously adding the phosphoramidite nucleoside monomer and tetrazole, a weak acid, to the reaction column. The tetrazole protonates the nitrogen of the phosphoramidite, making is susceptible to nucleophilic attack. This intermediate is so reactive that addition is complete within 30 seconds. The phosphoramidite is blocked at the 5'-OH with the dimethoxytrityl group.

The next step, capping, terminates any chains that did not undergo addition. Since the unreacted chains have a free 5'—OH they can be terminated or capped by acetylation. These unreacted chains are also called "failure products". Capping is done with acetic anhydride and 1-methylimidazole. Since the chains that reacted with the phosphoramidite in the previous step are still blocked with the dimethoxytrityl group, they are not affected by this step. Although capping is not ultimately required for DNA synthesis, it is highly recommend because it minimizes the length of impurities and thus facilitates their separation from the final product.

Finally, the internucleotide linkage is converted from the phosphite to the more stable phosphotriester. Iodine is used as the oxidizing agent and water as the oxygen donor. This reaction is complete in less than 80 seconds.

After oxidation, the dimethoxytrityl group is removed with a protic acid, either trichloroacetic or dichloroacetic acid. The cycle is repeated until chain elongation is complete. At this point, the oligonucleotide is still bound to the support with protecting groups on the phosphates and the exocyclic amines of the bases A, G, and C (T has no exocyclic amines). The oligonucleotide is cleaved from the support by a one-hour treatment with concentrated ammonium hydroxide. Ammonia treatment also removes the cyanoethyl phosphate protecting groups.

The protecting groups on the exocyclic amines of the bases are removed by treating the crude DNA solution in ammonium hydroxide at 55° C. If standard phosphoramidites are used, deprotection requires at least 8 hours at 55° C. IF FOD phosphoramidites are used, deprotection is complete in 1 hour at 55° C. or 8 hours at room temperature.

Figure 4:
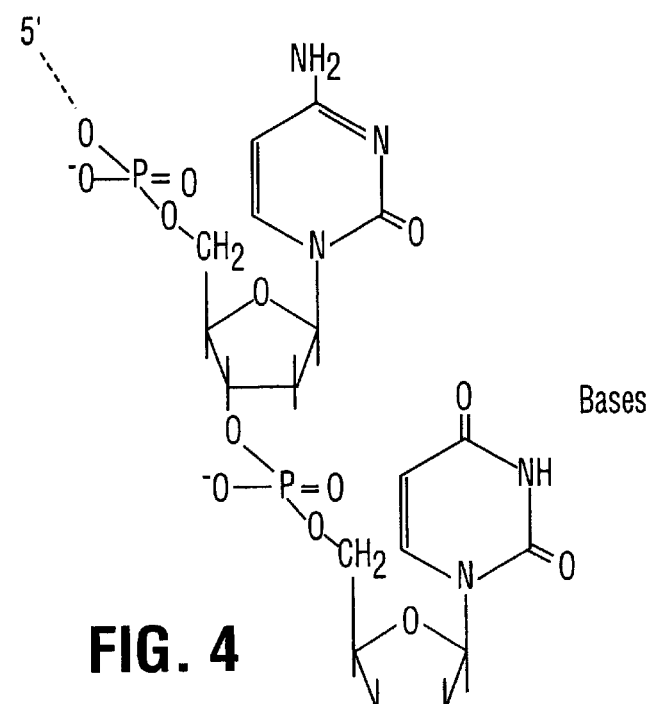
FIG. 4 is an illustration of a short section of DNA showing the phosphodiester bonds and the bases.
Figure 5:
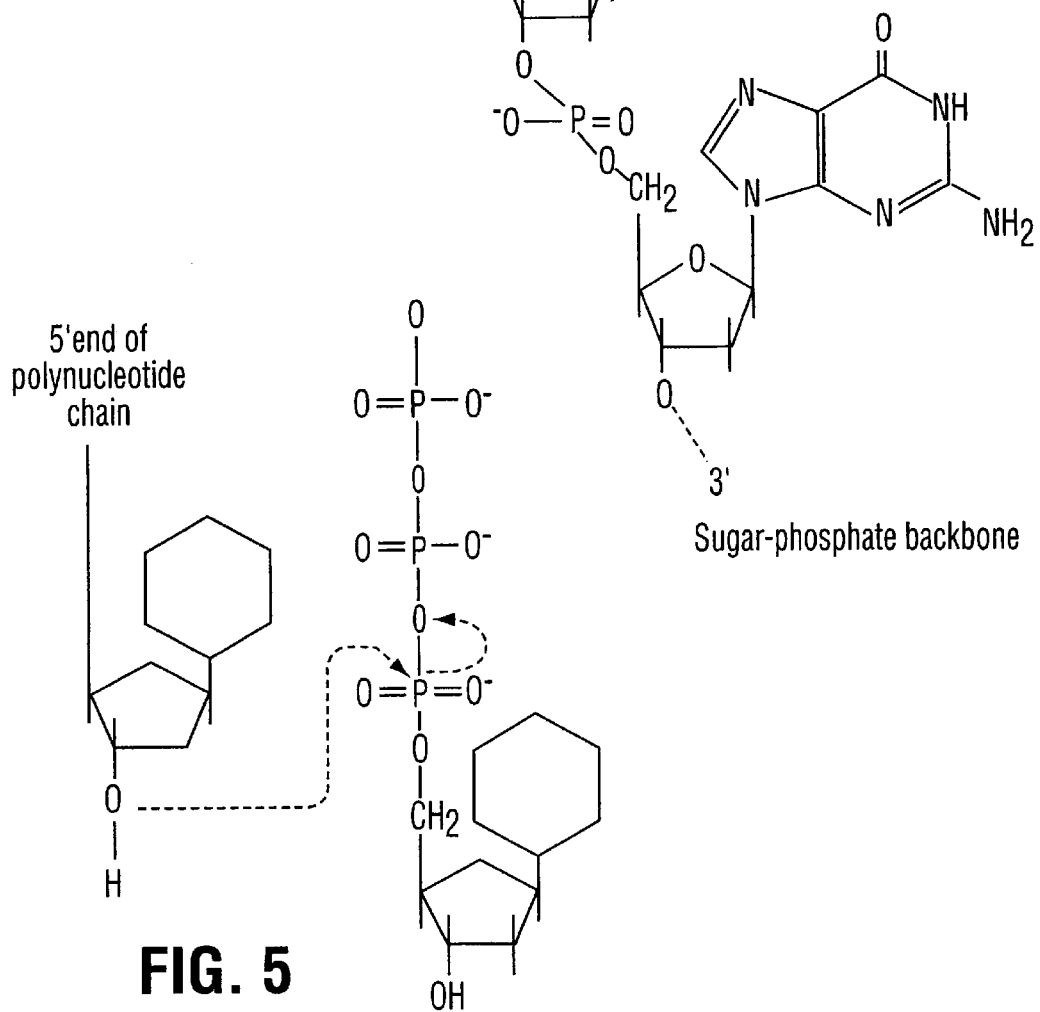
FIG. 5 is illustrates the formation of a phosphodiester bond by hydrophilic attack of the 3'—OH group of the last nucleotide of the chain on the 5' triphosphate of an incoming nucleotide, with release of pyrophosphate.

Using methods such as those indicated above, suitable intron-blockers are prepared. These blockers have oligonucleotides that are complementary to at least part of an intron and are preferably bordered at the 3'- and 5' ends by dideoxynucleotide tails. As shown in FIG. 4, a DNA strand comprises a chain of nucleotides joined by phosphodiester linkages of the 3'-hydroxyl group of the deoxyribose sugar of one nucleotide and the 5'-phosphate group of the adjacent nucleotide. As shown in FIG. 5, phosphodiester bond formation involves a hydrophilic attack by the 3'-OH group of the last nucleotide of the chain on the 5' triphosphate of the incoming nucleotide, with release of pyrophosphate.

Figure 6:
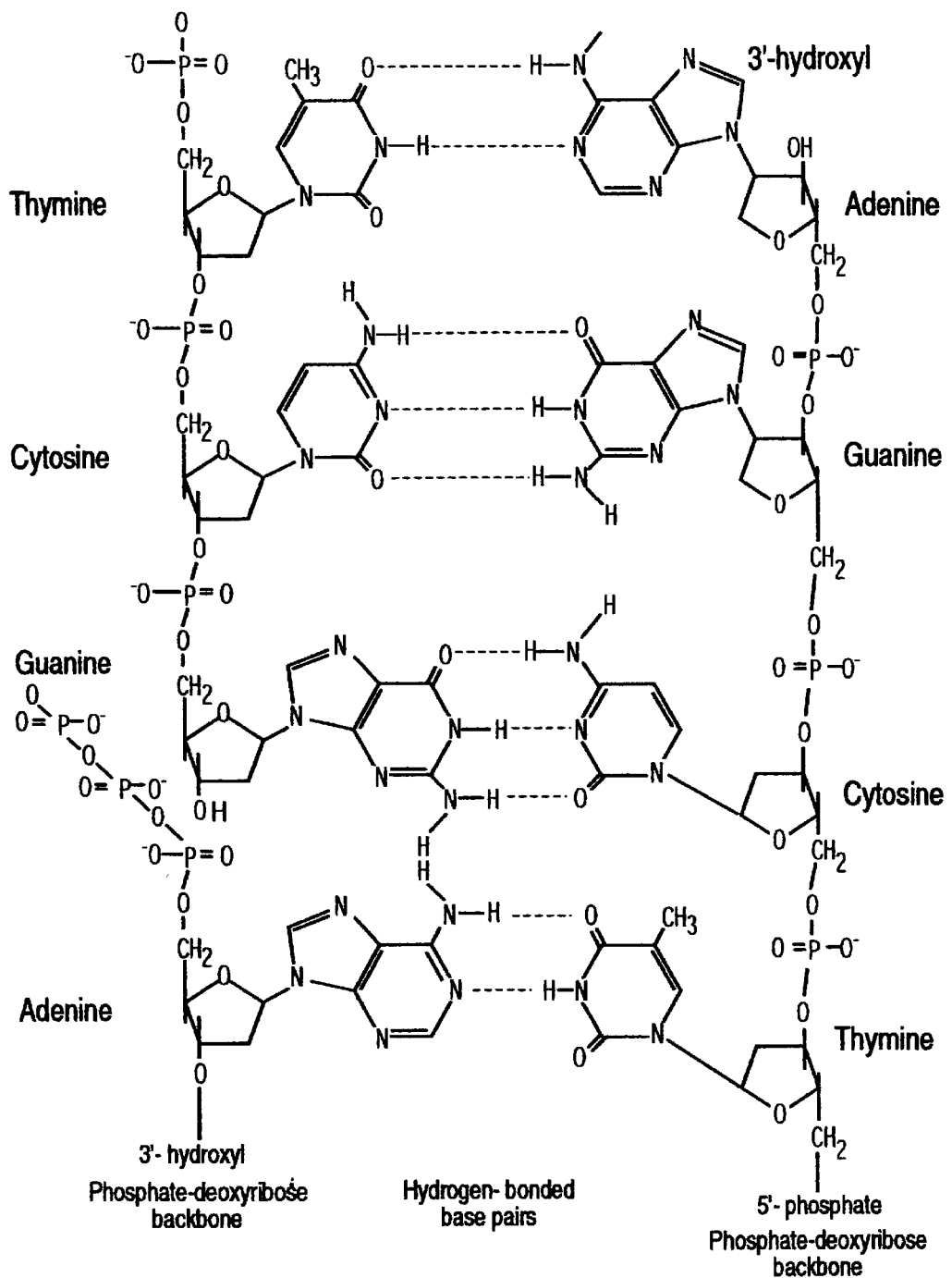
FIG. 6 illustrates the double helix structure of DNA showing how an incoming nucleotide is held by hydrogen bonding prior to the formation of the phosphodiester bond.

As shown in FIG. 6, during DNA synthesis an incoming nucleotide is directed by DNA polymerase to hydrogen bond with the complementary base of the template strand (annealing). As a result, this incoming nucleotide is in place to participate in phosphodiester linkage with the adjacent nucleotide of the growing chain.

The intron-blockers used in the present invention do not have to traverse the entire length of a target intron. Although there is no definite minimum or maximum size for the introns, usually the intron-blockers have a length of at least 15 nucleotides, and preferably 15–30 nucleotides. Only a single intron may be targeted in this way, or several may be targeted if desired for greater certainty. Of course, intron-blockers should be chosen to target the intervening intron region of the mRNA segment to be amplified by the RT-PCR.

The intron-blockers have termini that do not undergo chain extension. Chain extension may be prevented in several ways; for example, by employing nucleotides modified in one or more ways depending on whether the polymerase employed in any particular case has 3'–5' exonuclease activity (which is the case for natural polymerases), or whether it lacks such activity (which is the case for some genetically engineered polymerases). If the polymerase does not have 3'–5' exonuclease activity, chain extension may be prevented by employing oligonucleotides modified by or more of the following three methods:

1. by replacement of the —OH group at the $3^{rd}$ position of the last nucleotide at the 3'-end, resulting in non-availability of the hydroxyl group for phosphodiester fromation;

2. by removal or molecular change of the purine or pyrimidine base molecule of the last nucleotide at the 3'-end, resulting in a lack of annealing of the nucleotide at this end; or 3. by providing a non-phosphodiester bond between the penultimate and the final nucleotide at the 3'-end, creating stoichiometric constraints for purine or pyrimidine base pairing. The non-phosphodiester bond also ensures that the polymerase will not remove the unmatched nucleotide by 3'–5' exonuclease activity, since the 3'–5' exonuclease activity of polymerases is specific to phosphodiester bonds and will not affect other bonds. The nucleotide at the 5'-end should also preferably be bonded by a non-phosphodiester bond to avoid 5'–3' exonuclease activity of the polymerase. An example of a non-phosphodiester bond is a phosphomonoester bond in which the oxygen is attached to the last nucleotide via a single phosphate bond.

When the polymerase has 3'–5' exonuclease activity, chain extension may be prevented by employing oligonucleotides modified by or more of the following methods:

1. by replacement of the —OH group at the $3^{rd}$ position of the last nucleotide at the 3'-end, resulting non-availability of the hydroxyl group for phosphodiester formation; or 2. by removal or molecular change of the purine or pyrimidine base molecule of the last nucleotide at the 3'-end, and the formation of a non-phosphodiester bond between the penultimate and the final nucleotide a the 3'-end, preventing 3'–5' exonuclease activity.

Suitable methods for 3'-end labelling include the following:

1. Okayama, H. And Berg, P. (1982) Mol. Cell. Biol. 2, 161.

2. Flickinger, J., Gebeyehu, G., Buchman, G., Haces, R. and Rashtchian, A. (1992), Nucleic Acid Research, Vol. 20-9, p. 2382.

3. Collins, M. L. and Hunsaker, W. R. (1985) Anal. Biochem, 151, 211.

4. Molecular Cloning Vol 1,2,3 by Manniatis et al., Cold Spring Harbour, 1989.

The teachings of the above articles are incorporated herein by reference.

In the presence of the indicated intron-blockers, in-situ RT-PCR can be initiated and the mRNA derived cDNA template can be amplified without inaccuracies caused by genomic DNA ampification. Suitable methods are disclosed, for example, in:

1. Kolewicz, M., D'Alessco, J., Driftmier, R., Blodgett, K., and Gerad, G. (1985), Gene 35,249.

2. Molecular Cloning, Vol. 1,2,3, By Manniatis et al., Cold Spring Harbour, 1989.

3. Gerad, G., D'Alessco J., Kolewicz M., and Noon, M., (1986) DNA, 271.

The teachings of the above articles are incorporated herein by reference.

Once amplification of the cDNA of interest has been accomplished, its presence may be detected by any suitable means, for example:

1) By the size (length) of the DNA (as shown, for example, by gel electrophoresis).

2) By the restriction enzyme digestion pattern of the amplified DNA.

3) By designing labelled primers for the PCR amplification. Labelling may be either radioactive or non-radioactive ($^{32}P$, $^{35}S$ or biotin labels) and in both cases the labelled nucleotides are incorporated at the 5'-ends of the primers by $T_4$ polynucleotide kinase.

4) By using a third primer (i.e. a probe) that is either radioactively or non-radioactively labelled. Labelling of such a nucleotide may be carried out by either 3'-end labelling, 5'-end labelling or nick translation. These labelled probes may be used in identifying the amplified DNA by the Southern blot technique. The probe should preferably contain at least 15 nucleotides to bind to a specific region of the amplified DNA at ambient temperature.

The present invention can be used for amplifying, identifying and/or detecting most or all mRNA, provided such mRNA originates from genomic DNA incorporating at least two exons separated by at least one intron. Such identification and/or detection is useful for many diagnostic and testing purposes. The present invention can be used in any application in which the detection or identification of mRNA is instructive. The implementation of such an invention significantly advances the diagnostic capabilities and preventive measures of the medical profession and other diagnostic undertakings. Such applications include an enhanced ability to screen fetal cell samples for gene defects, research application in cell culture, assessing the expression of specific messages in immunology both in blood and in immune cells, biopsy material (including cancer), checking for expression of specific genes, forensic medicine as a negative control, detection of viral infections, e.g. in transplant organs, and disease-specific markers. For example, the present invention is particularly suited to the detection of maternal cell contamination in fetal cell samples, and a rapid molecular biology-based protocol for the detection of viral infections and cancer-associated genetic markers in donor transplant organs.

The present invention also has application in research applications in cell cultures; immunological assessment of specific messages in both blood and immune cells; assessment of biopsy material for detecting expression of specific genes; forensic medicine as a negative control; the detection of viral infection in transplant organs; identification of the expression of cancer genes or oncogenes in material from biopsies; detection of gene expression in pre-clinical and clinical trials involving animal models, human models and in vitro tissue culture models.

With regard to the application to the detection of viral infection in tissue transplants, it is to be noted that a major inherent limitation associated with organ transplant is the presence of human viral pathogens carried by the donor organs. These include HCV,HBV in liver infections, cytomegalovirus CMV in bone marrow and HCMV in lung transplant. Currently, donor organs do not undergo tests either before or after the transplant to detect such viral infections. Recent studies have shown that a significant percentage becomes infected after transplantation. Early detection of such viral infections would increase the efficiency of patient care, early recovery as well as decrease health care cost. The present invention may be used to provide such a test since mRNA characteristic of viral DNA be cellular genomic DNA, e.g. cellular-fos (c-fos). Gene amplification of the c-fos may be blocked by intron blockers and viral fos gene (v-fos) may be identified. This will be of use to identify viral infections which are associated with the onset of cancer, e.g. adenovirus. This will also help to detect viral infection in transplanted organs, e.g. cytomegalovirus. If the structure of the viral DNA is known (which is usual), suitable modified oligonucleotides may be developed without undue difficulty to act as the required intron-blockers to prevent the expression of identical cellular genes. Using the method of the invention, a test may be developed that would require less than four hours to indicate a result.

The invention can be illustrated in more detail by reference to its application to prenatal diagnosis. Prenatal diagnosis relies significantly at present on the technique of in-situ hybridization, using labelled oligonucleotide probes for the identification of gene defects in fetal cells. The present methodology is constrained by the occurrence of maternal cell contamination and the affinity of the oligonucleotide probes for such cells. Since maternal cells and fetal cells cannot be distinguished based on morphological characteristics, such contamination can lead to erroneous interpretation of results.

The present invention provides a means of genetically distinguishing fetal and maternal cells. Fetal cells express fetal cell specific proteins. Proteins such as alpha feto protein is not expressed in adult cells except in cases of some cancers. A pair of oligonucleotide primers are prepared for the detection of alpha feto protein expression. The complete structure polymorphism and novel repeat DNA elements have been revealed by a complete sequence of the human alpha-fetoprotein gene (Gibbs, et al., Biochemistry 26(5), 1332–1343, 1987) and the following introns have been revealed:

| Intron 1 | 812 bp |
|---|---|
| Intron 2 | 962 bp |
| Intron 3 | 2287 bp |
| Intron 4 | 1486 bp |
| Intron 5 | 918 bp |
| Intron 6 | 1548 bp |
| Intron 7 | 2275 bp |
| Intron 8 | 1657 bp |

Primers for RT-PCR are preferably designed across Intron 3 because a) large intron segments of approximately 2287 bp will reduce the chances of amplification of the genomic alpha feto gene segment, and b) the segment for RT-PCR amplification will be around 400 bp and thus easy to amplify.

Blocking oligonucleotide sequences are prepared on this basis with modified 3'- and 5'-nucleotides (lacking an —OH group at the $3^{rd}$ position of the ribose ring), e.g.:

First 5'-gaagagctattgtatgaaagaggga-3' [SEQ ID NO:1]

Second 5'-ccctccctgtgtccatgaaacatgg-3' [SEQ ID NO:2]

These primers function to inhibit the amplification of the genomic alpha feto gene. As a result, the cells which are subjected to amplification are distinguished from the contaminating maternal cells and identified as fetal cells. Accordingly, fetal cells are identified by the presence of alpha feto protein by RT-PCR identifying the message for alpha feto protein.

Following the identification of the fetal cells, the next step entails identifying the presence of genetic defects. The method of identification of specific genetic defects will vary according to the nature of the defect. Such defects may include point mutation, gene amplification, insertion, deletion, translocation, defection expression of fetal proteins, over expression of fetal proteins or expression of non fetal proteins. The methodology utilized in the identification of such defects may include in-situ hybridization, in-situ PCR and in-situ RT-PCR. The chosen detection system will employ the use of a labelled oligonucleotide.

A simple detection system according to the present invention employs a fluoro-red labelled oligonucleotide (such as Rhodamine-4-dUTP; Amersham Life Sciences) where the defective fetal cells will be visualized as having both a green signal and a red signal. Fetal cell assessment could be carried out according to the following chart:

| Signal in the cells | Inference |
| --- | --- |
| Green only | Fetal cells |
| Green and Red | Defective fetal cells |
| Red only | Defective maternal cells |
| No colour | Normal maternal cells. |

Figure 7:
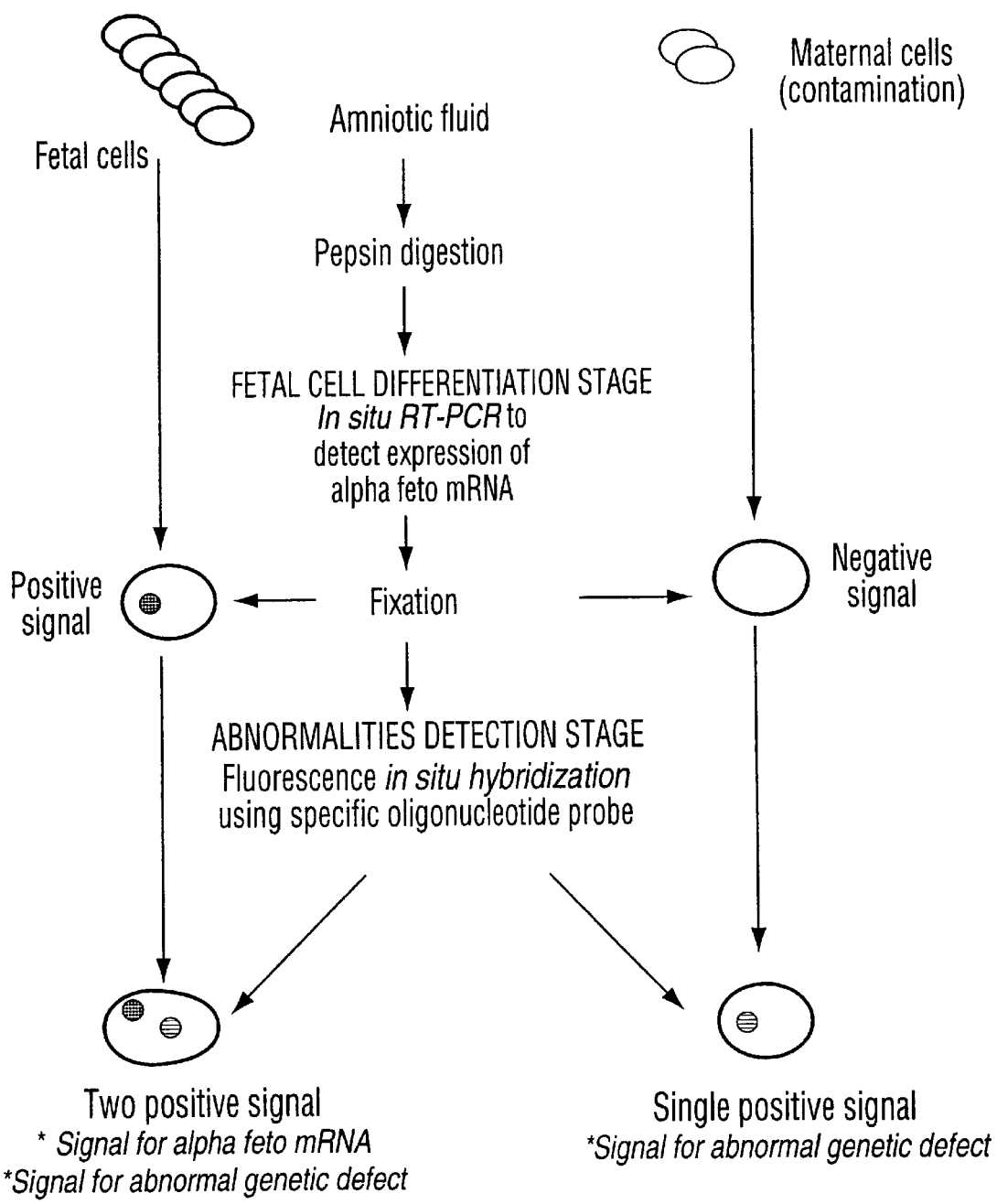
FIG. 7 shows a scheme for the determination of fetal genetic abnormalities using amniotic fluid on which the amplification process of the invention is carried out.

This protocol is illstrated in FIG. 7 and the practical details are provided in the following Example 1.

EXAMPLE 1

In-situ RT-PCR using modified dideoxy oligonucleotides used to differentiate fetal cells in maternal cell contaminated amniotic fluid sample.

Fixation of Cells or Tissues

Cells from an amniotic fluid sample are suspended in 10% formalin, phosphate buffer is added and the sample is incubated for more than 16 hours. The cells are then washed with DEPC water twice and air dried. The cell concentration is 5000 to 10,000 cells in 10–100 $\mu l$ of volume.

Pepsin Digestion

Pepsin solution is prepared freshly by dissolving 20 mg of pepsin powder in 9.5 ml of DEPC treated water (this requires about 5 minutes). HCl (0.2 M, 0.5 ml) is added to form a solution of 2 mg in 0.01 M HCl. Mounted slides are mounted in a food saver with wet paper tissues. The pepsin solution is added to cover the cell area and the food saver is covered and allowed to stand at room temperature for 40–75 minutes, depending on the cell type and type of fixation. The slides are then washed by dripping in water for 1 minute followed by washing in 100% ethanol for 1 minute.

Reverse Transcription

A reverse transcription mixture is prepared containing the following ingredients:

| | Per Slide |
| --- | --- |
| 5 X RT buffer | 10 $\mu l$ |
| DTT 0.1 M | 5 $\mu l$ |
| dT 10 $\mu M$ | 2.5 $\mu l$ |
| dNTP 10 $\mu M$ | 2.5 $\mu l$ |
| Superscript (Reverse Trascriptase) | 0.5 $\mu l$ |
| DEPC water | 29.5 $\mu l$ |

The mixture is added to the cells and incubated at 37° C. (or 42° C.) for 30–40 minutes in a plastic box with paper tissue. The incubate is then washed with DEPC water for 1 minute, with 100% ethanol for 1 minute and air dried.

Polymerase Reaction

A PCR mixture is prepare as follows:

| | Per Slide | |
| --- | --- | --- |
| 10 X PCR | 15 $\mu l$ | |
| MgCl$_2$ | 20 $\mu l$ | |
| dATP | 3 $\mu l$ | |
| dGTP | 3 $\mu l$ | |
| dCTP | 2.7 $\mu l$ | |
| primer* 1 20 $\mu M$ | 3 $\mu l$ | alpha feto protein |
| primer 2 20 $\mu M$ | 3 $\mu l$ | |
| Taq polymerase | 0.5 $\mu l$ | |
| Modified dideoxyoligonucleotide | 2 $\mu l$ | |
| DEPC water | 93.3 $\mu l$. | |

*The oligonucleotide is labelled with Fluoro Green (Fluorescein - 11-dUTP; Amersham Life Sciences RPN 2121).

The assembly tool is turned on to 72° C. and the PCR cycler is turned on and set to 70° C. PCR mixture (50 $\mu l$) is placed on each spot and the assembly is slid upon the PCR. After PCR there is no bubble count.

Detection

The fluorescent signal from the labelled probe is visualized by eye or is analysed by CCD camera or a confocal microscope. The cells which exhibit green fluorescence are the cells showing the target mRNA (the cells expressing alpha feto protein). Those cells not exhibiting the green fluorescence are maternal cells. Hence, the degree of maternal cell contamination may be determined.

Having identified the fetal cells, the next step is to identify any genetic defects in the cells. The method of identification of genetic defects will vary according to the nature of the genetic defect of immediate concern. The methods that may be used include the following:

a) Point mutation
b) Gene amplification
c) Insertion
d) Deletion
e) Translocation
f) Defection expression of fetal proteins
g) Over expression of fetal proteins
h) Expression of non-fetal proteins.

The methodology involved in the identification of such defects may include the following:

a) In-situ hybridisation
b) In-situ PCR
c) In-situ RT-PCR.

In any such method, the detection system will normally have a labelled oligonucleotide probe. A simple detection system may involve using a fluoro-red label (Rhodamine-4-dUTP; Amersham Life Sciences), in which case the defective fetal cells exhibit a red signal.

EXAMPLE 2

Approach

An experiment was designed to demonstrate the selective inhibition of intron blockers. This experiment was based on human alpha feto gene and involved the preparation of intron blockers designed to bind to the intron region of the gene and to block the amplification of that region by PCR. Since the corresponding mRNA does not carry the intron region, the intron blockers will not inhibit the amplification of the RT-PCR based on the mRNA derived cDNA template.

Experimental Detail

A) Partial Nucleotide Sequence of Human Alpha Feto Gene

The DNA sequence is disclosed by Gibbs et al., Biochemistry (26) 1987, (1332–43) and is shown as follows [SEQ ID NO:3]:

Exon 9 →
PCR forward primer
5'-T TTT GTT CAT GAA TAT TCA AGA AGA CAT CCT CAG CTT GCT GTC
TCA GTA ATT CTA AGA GTT GCT AAA GGA TAC CAG GAG TTA TTG GA
AAG TGT TTC CAG ACT GAA AAC CCT CTT GAA TGC CAA GAT AAA INTRON 9 →
GGAgtaagttgctctagaatttagggagtatgaaaaactggattgatatctatctgttaaa
aatgctgtttgtttgaaagcctctaagttttcaactagttgttagccagttatatctatttgt INTRON BLOCKER 2 N
ctagatattaagctgttattaactagcagtcagcagctagtggcttgttttagaaacaaa INTRON BLOCKER 1 N
atgttaattgcttctcagcctttggctaagatcaagtgtagaaataaaaatgttaaccaaa
agtcctttgatccacaaataaaggtagtattcattattcattttttggataacttcagaaagg
caagaatttggtacagaaagaactgtaaccatttatccaaagattgagttttgccattaaat
gattttgtgatttataaaatgttaaacttaatctccccaaaatccattttctgtaattatca
aaatttacactttaccatatttaatatttaaacatctctgattggttttataatagtatata
atattgatcaattttatatacaaagttatgcatccaagaaaagaaaaatgtatatgtaataa EXON 10 →
ttcttcattttcagGAA GAA GAA TTA CAG AAA TAC ATC CAG GAG AGC CAA
GCA TTG GCA AAG CGA AGC TGC GGC CTC TTC CAG AAA CTA GGA GA
TAT TAC TTA CAA AAT GC-3'
PCR reverse primer PCR primer sequences are underlined in exon 9 and exon 10 regions. Intron blocker regions are underlined in the intron 9 region.

B) Labelling of the 3-End of Intron Oligonucleotide With Dideoxy Thymidine Triphosphate (ddTTP)
Intron blocking sequence 2 N:

5'-cagtcagcagctagtggcttgc-3' [SEQ ID NO:4]

Intron blocking sequence 1 N:

5'-cacttgatcttagccaaaaggc-3' [SEQ ID NO:5]

50 μl of a reaction mixture was made as follows:

| | |
|---|---|
| Intron primer (10 pmol/μl) | 7.5 μl |
| 10 X Transferase buffer | 5.0 μl |
| ddTTP (5 nM) | 10.0 μl |
| Transferase 16 units/μl | 3.0 μl |
| Water | 24.5 μl |

The mixture was incubated at 37° C. for 15 minutes and then 5 μl of 0.2M EDTA was added to stop the reaction. The mixture was then heated at 95° C. for 5 minutes.

C) Purification of Labelled Primer

The labelled primer was purified using QIAgen™ (California, U.S.A.) nucleotide removal kits.

10 volumes of buffer PN to 1 volume of the reaction sample was added and mixed. A QIAquick™ spin column was placed in a 2 ml collection tube. The sample was applied to the spin column and centrifuged at 6000 rpm for 1 minute. The follow-through was discarded and the QIAquick™ column was placed in the same collection tube. 750 μl of buffer PE was added to the column and centrifuged at 6000 rpm for 1 minute. The flow-through was discarded. A QIAquick™ column was placed back in the same tube and centrifued for another additional 1 minute at 13,000 rpm. A QIAquick™ column was placed in a 1.5 ml micro centrifuge tube. The DNA was eluted by adding 100 μl of sterile water to the center of the QIAquick™ spin column, allowed it to stand for 1 minute and then centrifuged for 1 minute at 13,000 rpm.

D) Extraction of Alpha Feto Total RNA From Heptoma Cells Grown in Monolayers

250 μl of the cell suspension was added to 750 μl of Trizol™ reagent (Gibco) and was left at room temperature for 5 minutes. 200 μl of chloroform was added and mixed well for 15 seconds. The mixture was centrifuged at 12,800 rpm at +4° C. for 10 minutes. The upper aqueous layer was transferred into a new 1.5 ml eppendorf tube. 500 μl of isopropanol was added and mixed. The mixture was left at room temperature for 5 minutes, and then centrifuged at 12,800 rpm at +4° C. for 10 minutes. The supernatant was discarded and 200 μl of 85% alcohol was added. The mixture was centrifuged at 12,800 rpm at +4° C. for 10 minutes. The supernatant was discarded and the tubes were air dried. The total RNA was suspended in 20 μl of diethylpyrocarbonate (DEPC) treated water.

E) Reverse Transcription of Alpha Feto mRNA Template

Total RNA was extracted using Trizol™ methods and reagents recommended by the manufacturer as in (D). The following were then mixed in a 1.5 ml centrifuged tube:

| | |
|---|---|
| Total RNA 1 μg | 2 μl |
| Downstream primer (10 pM/μl) | 2 μl |
| Water | 8 μl. |

The mixture was heated at 70° C. for 10 minutes and then, to the heated mixture, were added:

| | |
|---|---|
| 5 X 1st strand synthesis buffer | 4 µl |
| dNTP (10 mM) | 1 µl |
| 0.1 MDTT | 2 µl. |

The mixture was heated at 42° C. for 2 minutes. 1 µl of Superscript II™ was added to the above mixture, and the mixture was incubated at 42° C. for 50 minutes. The reaction was then stopped by heating at 70° C. for 10 minutes.

F) Extraction of DNA From Human Blood Cells

DNA was extracted using a QIAgen™ DNA extraction kit. 200 µl of whole blood was placed in a micro centrifuge tube and 25 µl of QIAagen™ proteinase K and 200 µl of µL buffer was added. The sample was incubated at 70° C. for 10 minutes. 210 µl of ethanol (95–100%) was added to the sample and mixed again by vortexing. A QIAamp™ spin column was placed in a 2 ml collection tube and the mixture resulting from the ethanol addition and vortexing was added to the column and spun for 1 minute at 8000 rpm. The filtrate was discarded and the spin column was placed in a new 2 ml collection tube. 500 µl of AW buffer was added and centrifuged at 8000 rpm for 1 minute. The filtrate was discarded and the spin column was placed in a new tube and another 500 µl of AW buffer was added and centrifuged at 13,000 rpm for 2 minutes and the filtrate discarded. A QIAquick™ spin column was placed back into the empty collection tube and centrifuged at 13,000 rpm for 1 minute. The spin column was placed in a clean micro centrifuge tube and 200 µl of distilled water pre-heated to 70° C. was added. The mixture was allowed to stand at room temperature for 1 minute and then centrifuged at 8,000 rpm for 1 minute.

G) Polymerase Chain Reaction

A polymerase chain reaction was carried out using the following Alpha feto PCR primers:

a) 5'-tttgttcatgaatattcaagaaga-3' [SEQ ID NO:6]

b) 5'-attttgtaagtaatattctcctag-3' [SEQ ID NO:7].

PCR was carried out both with and without intron blockers.

i) Without Intron Blockers

The reaction was carried out in 25 µl of the following reaction mixture:

| | |
|---|---|
| dH$_2$O | 16.0 µl |
| Template (50 ng/µl) | 2.0 µl. |

The mixture was heated to 95° C. for 10 minutes. The master mix was prepared as follows:

| | |
|---|---|
| Primer 1 (10 pmol/µl) | 5 µl |
| Primer 2 (10 pmol/µl) | 5 µl |
| dNTP (10 mM) | 2.5 µl |
| 10 X Buffer | 2.5 µl |
| MgCl$_2$ 25 mM | 7.5 µl |
| Taq 5 U/µl | 2.5 µl. |

7.0 µl of this master mix was added.

PCR was carried out in a Gene Amp 2400™ thermocycler (Perkin and Elmer) on the following cycle protocol:

| | |
|---|---|
| 94° C./15 sec | |
| 45° C./20 sec | |
| 72° C./25 sec | |
| Number of cycles | 35 |
| Extension | 72° C. for 10 minutes. | ii) With Intron Blockers

The reaction was carried out in 25 µl of the following reaction mixture:

| | |
|---|---|
| dH$_2$O | 12.0 µl |
| Template 50 ng/µl | 2.0 µl |
| Intron blocker 1 N (10 pM/µl) | 2.0 µl |
| Intron blocker 2 N (10 pM/µl) | 2.0 µl. |

The mixture was heated to 95° C. for 10 minutes. A master mix was prepared as follows:

| | |
|---|---|
| Primer 1 (10 pmol/µl) | 5 µl |
| Primer 2 (10 pmol/µl) | 5 µl |
| dNTP (10 mM) | 2.5 µl |
| 10 X Buffer | 2.5 µl |
| MgCl$_2$ 25 mM | 7.5 µl |
| Taq 5 U/µl | 2.5 µl. |

7.0 µl of this master mix was added.

The PCR was carried out in a Gene Amp 2400™ thermocycler (Perkin and Elmer) on the following cycle protocol:

| | |
|---|---|
| 94° C./15 sec | |
| 45° C./20 sec | |
| 72° C./25 sec | |
| Number of cycles | 35 |
| Extension | 72° C. for 10 minutes. |

DNA electrophoresis was then carried out as follows. The amplified products were separated on a horizontal electrophoresis apparatus (Tyler Research) using 1.5% agarose in TBE buffer at 5V/cm voltage gradient. The gels were stained with ethidium bromide (0.5 µg/ml) and destained with water for 30 minutes. The gel was visualized under UV 312 nm and photographed with a Polaroid™ camera.

H) Results

Figure 8:
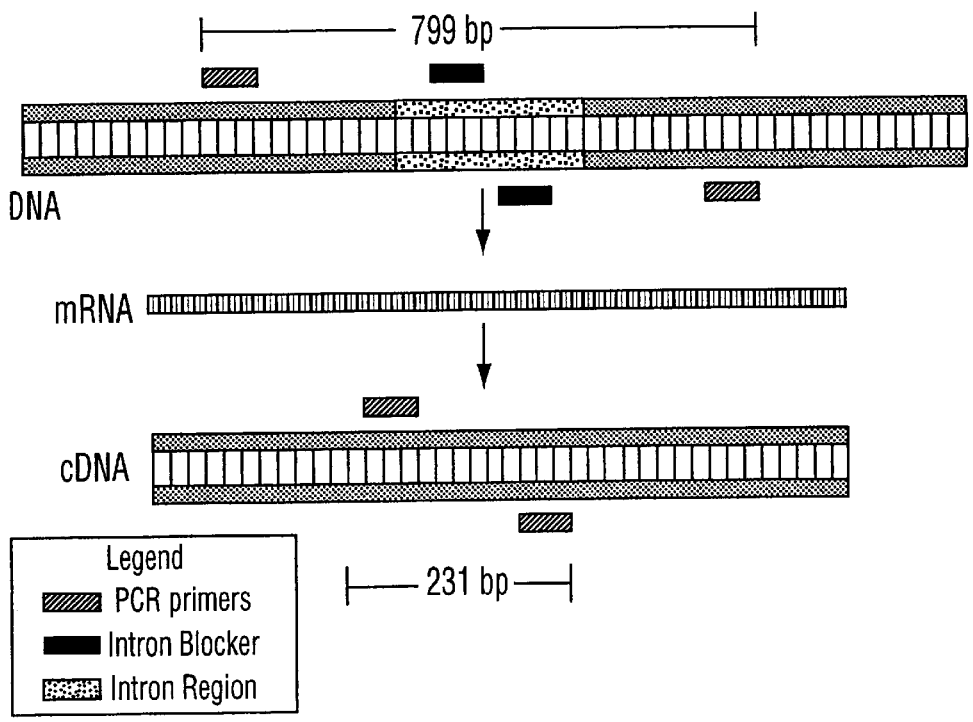
FIG. 8 is an illustration of the templates, primers and blockers used in the experiment of Example 2.
Figures 9A, 9B, 9C, 9D, 9E:
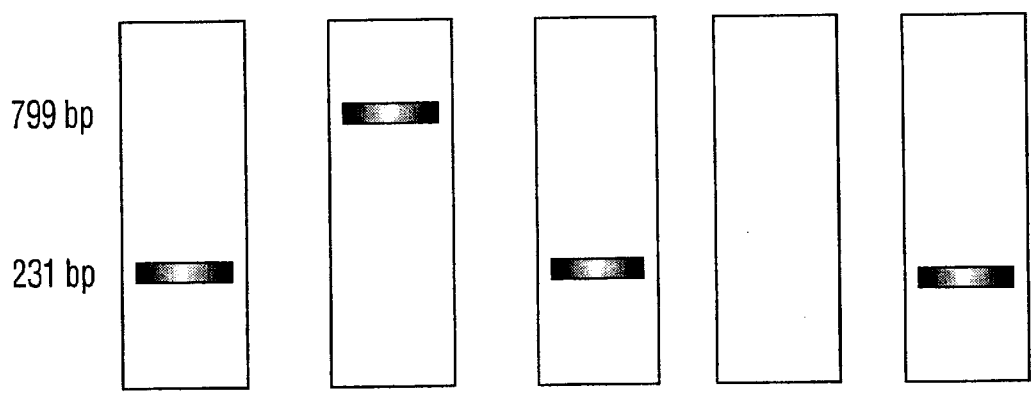
FIGS. 9(A), 9(B), 9(C), 9(D) and 9(E) are representations of gel electrophoresis results of Example 2, showing the selective inhibition of PCR based on human alpha feto gene DNA but not the RT-PCR based on an mRNA derived cDNA template of the alpha feto gene.

The results of this experiment are illustrated in FIGS. 8, 9(A), 9(B), 9(C), 9(D) and 9(E). FIG. 8 illustrates the DNA and mRNA of the alpha feto gene and the intron region of the gene, as well as the primers and blockers used in the Example. The target sequences for amplification (799 bp in the DNA template and 231 bp in the cDNA template) are shown. The five vertical columns of FIGS. 9(A), 9(B), 9(C), 9(D) and 9(E) represent the results of gel electrophoresis showing the amplified sequences, as follows:

9(A) shows the result of using cDNA as a template. Only the 231 bp fragment is amplified, as would be expected.

9(B) shows the result of using DNA as a template without intron blockers. As would be expected the 799 bp sequence has been amplified.

9(C) shows the result of using cDNA as a template in the presence of intron blockers. There is no inhibition of the amplification of the 231 bp sequence since the blockers do not bind to this region (intron absent).

9(D) shows the result of using DNA as a template in the presence of intron blockers. There is no amplification of the 799 bp fragment, showing that the blockers bind to the intron region and prevent the PCR reaction.

9(E) shows the result of using cDNA and DNA as templates in the presence of intron blockers. There is no inhibition of the amplification of the 231 bp fragment, but no amplification of the 799 bp fragment. This shows the effectiveness of the present invention.

I) Conclusion a) The designed set of primers amplifies a segment of human alpha feto protein gene which is about 799 bp in length. The same set of primers amplifies a segment (about 231 bp) of the alpha feto protein mRNA via RT-PCR. Both the amplifications were carried out under identical thermocycling conditions using identical reagents.

b) Amplifications of alpha feto gene segment is inhibited by incorporating the intron blockers in the PCR mixture. However, the amplification of the segment of alpha feto mRNA via RT-PCR was not inhibited by the intron blockers.

EXAMPLE 3

Identification of Maternal Cell Contamination

An example of extending the above principle to a practical situation involves the identification of maternal cell contamination.

Figure 10A:
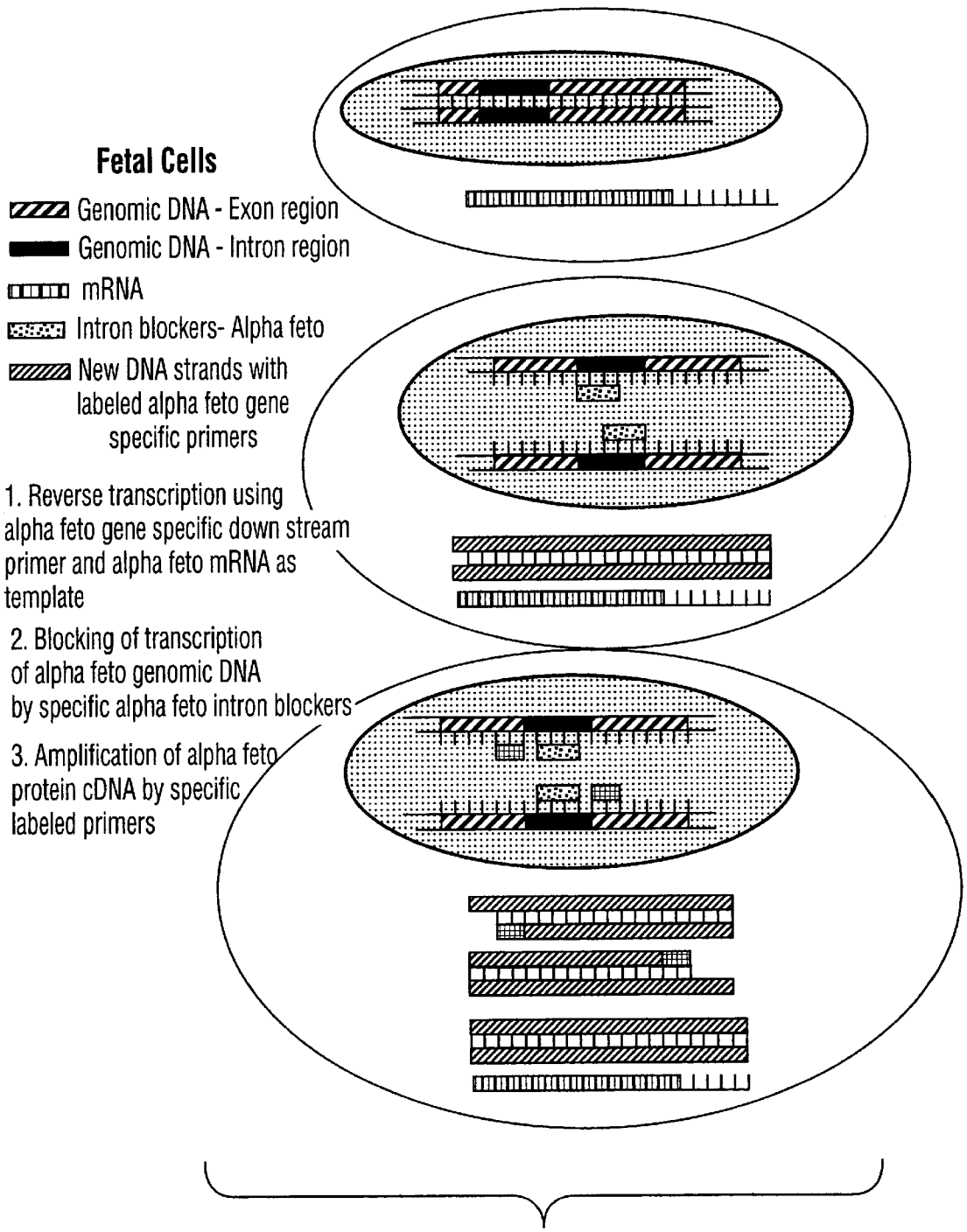
FIGS. 10(A) and 10(B) are schematic diagrams showing the use of intron blockers to prevent the amplification of maternal alpha feto gene DNA (FIG. 10(B)) while allowing the amplification of fetal cDNA (FIG. 10(A)).
Figure 10B:
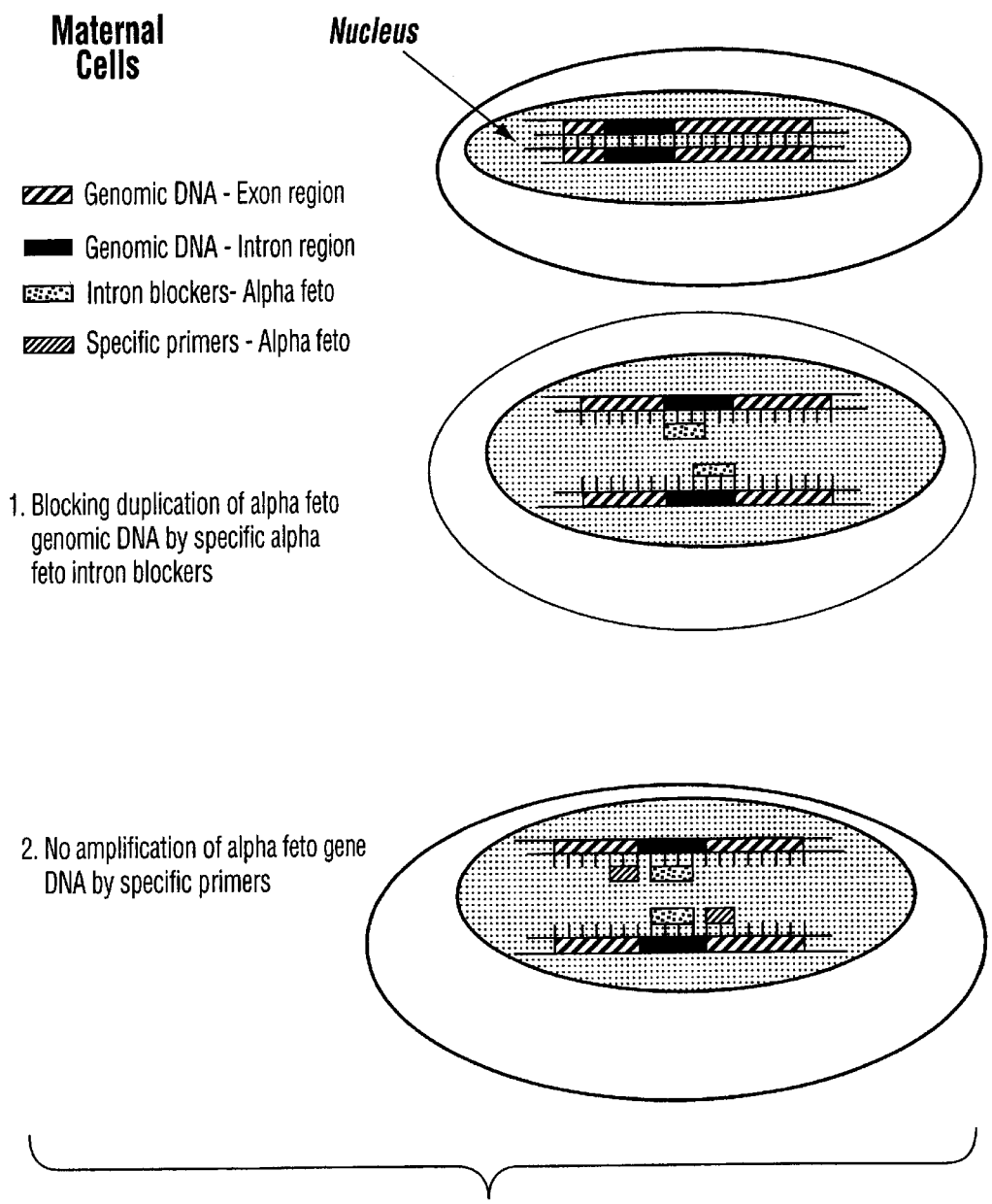

In-situ RT-PCR is carried out on a chorionic villi sample (CVS) using the above-mentioned intron blockers and fluorescent-labelled nucleotides. Fluoroescence is seen only in the fetal cells based on the amplification of the cDNA, and there is no fluorescence in the maternal cells because the maternal cells lack expression of the alpha feto gene. It is to be noted that the genomic alpha feto gene in both the maternal cells and the fetal cells is inhibited by the intron blockers, as illustrated in FIG. 10(A) for the fetal cells, and FIG. 10(B) for the maternal cells.

The invention and its preferred embodiments have been described in detail above. However, it will be apparent to persons skilled in the art that various modifications and alterations will be possible without departing from the scope of the invention as defined by the appended claims.

What we claim is:

1. A polynucleotide consisting of SEQ. ID NO:1 having nucleotides at the 3'- and 5'-ends thereof modified to prevent chain extension during reverse transcriptase polymerase chain reaction.

2. A polynucleotide consisting of SEQ ID NO:2 having nucleotides at the 3'- and 5'-ends thereof modified to prevent chain extension during reverse transcriptase polymerase chain reaction.

3. A polynucleotide consisting of SEQ ID NO:4 having nucleotides at the 3'- and 5'-ends thereof modified to prevent chain extension during reverse transcriptase polymerase chain reaction.

4. A polynucleotide consisting of SEQ ID NO:5 having nucleotides at the 3'- and 5'-ends thereof modified to prevent chain extension during reverse transcriptase polymerase chain reaction.

* * * * *

UNITED STATES PATENT AND TRADEMARK OFFICE
CERTIFICATE OF CORRECTION

PATENT NO. : 5,994,528

DATED : November 30, 1999

INVENTOR(S) : Thuraiayah Vinayagamoorthy, et al.

It is certified that error appears in the above-identified patent and that said Letters Patent is hereby corrected as shown below:

Column 1, delete lines 10-12, and insert therefore --This application is a division of application number 08/929,302, filed September 11, 1997 (pending), and claims the priority right of application number 60/027,370, filed herein (abandoned).--

Signed and Sealed this

Fifth Day of December, 2000

Attest:

Attesting Officer

Q. TODD DICKINSON

Director of Patents and Trademarks